United States Patent [19]

Hebborn

[11] 4,000,263
[45] Dec. 28, 1976

[54] ERYTHROMYCIN SOLUTION

[75] Inventor: Peter Hebborn, Clarence, N.Y.

[73] Assignee: Westwood Pharmaceuticals, Inc., Buffalo, N.Y.

[22] Filed: May 2, 1975

[21] Appl. No.: 574,055

[52] U.S. Cl. .................................. 424/181; 536/9
[51] Int. Cl.$^2$ ...................................... A61K 31/71
[58] Field of Search ................ 260/210 E; 424/181

[56] References Cited

UNITED STATES PATENTS 3,780,737   12/1973   Banford ........................... 424/181

OTHER PUBLICATIONS

Chem. Abstracts, vol. 51, 1957, 10642e.

*Primary Examiner*—Lewis Gotts
*Assistant Examiner*—Cary Owens
*Attorney, Agent, or Firm*—Irving Holtzman; George A. Mentis; David J. Mugford

[57] ABSTRACT

There is disclosed a storage stable solution comprising a solution of erythromycin, propylene glycol, ethyl alcohol, and an ethoxylated ether of lauryl alcohol. The solution possesses excellent stability at both room temperature and at elevated temperatures for prolonged periods of time.

3 Claims, No Drawings

ERYTHROMYCIN SOLUTION

This invention relates to a pharmaceutical composition useful in the treatment of acne and, more particularly, to such a composition in the form of a solution of erythromycin possessing high storage stability.

Acne is a condition of the human skin characterized by an excessive flow of sebum, or skin oil, from the sebaceous glands. It is one of the traumatic conditions which is often a consequence of puberty. In moderate to severe cases, which can last past the third decade of life, severe pitting and disfigurement of the skin of the back and face can result. The juvenile afflicted with acne on the facial areas may be so sensitive and self-conscious about the vulgar appearance of the disease, that severe psychic trauma may result.

Various forms of therapy for the treatment of acne have been investigated, including dietary regimens, i.e., the avoidance of sweets, fatty foods and particularly chocolate, the use of birth control pills to correct hormonal inbalance, and the use of topical treatments such as rigorous multi-daily washing of the affected areas with soap and water and the use of medicines such as sulfur-salicylic acid preparations to dry and desquamate the skin.

Various authorities have reported that certain antibiotics when taken orally reach the skin in sufficient concentration to permit a response of the skin and the skin flora to the antibiotic. Thus, Strauss, et al reported in the *Journal of Investigative Dermatology*, Volume 47, No. 6, pages 577–581(1966) that the oral administration of large doses of antibiotics such as erythromycin results in a decrease of sebum acidity.

It is known that resident bacteria live on or near the surface in the desquamating portion of the horny layer of the skin. Therefore, for an antibiotic to be effective when taken orally, it is necessary that an effective amount of the drug reach the epidermis to combat the bacteria residing therein. This requires very large dosages of the antibiotics. Livinggood, et al reported in *J. Am. Med. Assoc.*, Volume 153, pages 1266–1270 (1953) on the treatment of various cutaneous bacteria infections using antibiotic ointments including erythromycin preparations. The ointments used included white petrolatum, a wool fat-petrolatum base, a cholesterol-petrolatum base, and a hydrophilic ointment containing hydroxyl animal fats.

It would be advantageous to apply an antibiotic directed to the desired site of action, i.e., directly to the skin tissue in the treatment of acne. However, it has been shown that ampicillin, erythromycin, and tetracycline penetrate poorly through the skin, *Chem. Abstracts*, Vol. 72, 103668Q (1970).

Erythromycin has been shown to have a low order of toxicity to the skin tissues as reported by J. C. Lawrence in *Brit. J. Pharmacology*, 14, 168 (1959). However, it has low stability in solution — i.e., at 18°–22° C., it has a stability of only about 2 weeks; A. B. Chernomordik, *Aptechn, Delo.*, 10, 58 (1961); *Chem. Abst.* 60, 14337[e] (1964).

Polyvinyl alcohol has been reported to increase the stability of erythromycin in aqueous solutions; *Chem. Abstracts*, 64, 14836[d] (1966). Moreover, erythromycin has a low order of solubility in water; U.S. Pat. No. 3,764,595. It is known that erythromycin exhibits greater solubility in polyethylene glycol in water; *Chem. Abstracts*, 51, 10642[e] (1957).

The incorporation of erythromycin into lipophillic bases, e.g., a lanolin-petrolatum mixture and/or into compositions containing cocoa butter, increases the stability of the erythromycin; *Chem. Abstracts* 79, 83450[b] (1973) and C. N. Blissert, *J. Pharm. Sciences*, 50, 56 (1961). However, when the erythromycin is suspended in a lipophillic material, the release of the drug is adversely affected. In such a medium, the release of the drug is a function of its water solubility and, because of the limited water solubility of erythromycin, such formulations are not satisfactory; *Chem. Abstracts* 70, 80819[g] (1969) and 78, 164019[z] (1973). Further, the use of greasy water-repelling substances is not appropriate for acne therapy.

It is an object of this invention to provide a solution of erythromycin which is stable at room temperature and at elevated temperatures for prolonged periods.

It is another object of this invention to provide such a solution which is useful for the treatment of acne.

It has now been discovered that when erythromycin is dissolved in a composition comprising propylene glycol, ethyl alcohol, and an ethoxylated ether of lauryl alcohol, the resulting erythromycin solution possesses excellent stability at both room temperature and at elevated temperatures for prolonged periods of time. The erythromycin is preferably present in the solution in an amount of about 0.5 to 3.0% by weight, the propylene glycol in an amount of about 35 to 45% by weight, the ethoxylated ether of lauryl alcohol in an amount of about 4 to 10% by weight and the ethyl alcohol in quantities sufficient to make up 100% of total constituents.

Ethoxylated ether of lauryl alcohol is sold under the trade names Brij-30 and Laureth-4 and has the chemical formula $CH_3(CH_2)_{10}CH_2(OCH_2CH_2)_nOH$ wherein R has an average value of 4. The ethyl alcohol is preferably specially denatured alcohol. The erythromycin used is erythromycin base, a term used to distinguish it from the several derivatives of erythromycin. The amount of erythromycin used is dependent upon the potency as is illustrated in the example.

The erythromycin solution may be applied to the portion of the skin of a patient affected by acne by rubbing the solution thereon to form a thin layer from which the volatile constituents can readily evaporate. The solution contains good antibacterial activity and retains its ability to penetrate the skin and its antibacterial activity even after long periods of storage at room temperature or at elevated temperatures.

The following example illustrates the practice of this invention:

EXAMPLE

A composition was prepared comprising 40.00% by weight of propylene glycol, 6.00% by weight of Brij-30, 2.23% by weight of erythromycin base and 51.77% by weight of specially denatured alcohol. The erythromycin base which was used had an assay potency of 896 micrograms per milligram (89.6% active). Thus, 2.23% by weight of erythromycin base corresponded to an actual concentration of 1.9981% of 100% active erythromycin. Stability tests were conducted on the erythromycin solution by storing samples of the formulation at 35° and at 45° C. with aliquots being taken at appropriate intervals. Microbiological assays were performed on the aliquots in the manner approved for erythromycin by the Food and Drug Administration. This method is described in the Federal Registry, Title 21, parts 141 and 148e. In the following table, the five-digit assay figures refer to micrograms per milliliter of activity, and the figure in parentheses following a particular assay refers to the percent loss or gain in potency after storage for the indicated period. The experimental error for the assay is ± 6%. The original assay, i.e., at time zero and room temperature, was 16,412 mcg/mg.

TABLE

| Storage Time | Temperature | Assay mcg/ml (% gain or loss) |
|---|---|---|
| Two weeks | 37° | 16,412 (0) |
| | 45° | 17,704 (+7.3) |
| Four weeks | 37° | (Not assayed) |
| | 45° | 17,768 (+7.6) |
| Six weeks | 37° | 16,871 (+2.45) |
| | 45° | 16,517 (+0.6) |
| Eight weeks | 37° | (Not assayed) |
| | 45° | 15,640 (−4.85) |
| Ten weeks | 37° | 17,308 (+5.05) |
| | 45° | 15,598 (−5.00) |
| Twelve weeks | 37° | (Not assayed) |
| | 45° | 17,120 (+4.15) |
| Fourteen weeks | 37° | (16,079 (−2.0) |
| | 45° | (Not assayed) |
| Sixteen weeks | 37° | (Not assayed) |
| | 45° | (Not assayed) |
| Eighteen weeks | 37° | 15,558 (−5.21) |
| | 45° | (Not assayed) |
| Twenty weeks | 37° | 15,642 (−4.44) |

TABLE-continued

| Storage Time | Temperature | Assay mcg/ml (% gain or loss) |
|---|---|---|
| | 45° | (Not assayed) |

The 45° sample was not assayed after 12 weeks due to an insufficient supply of sample stored at that temperature. The above results of elevated temperature stability are unusual for an erythromycin formulation. This data indicates that the formulation will probably retain its potency for three years.

What is claimed is:

1. An erythromycin solution which possesses good storage stability comprising a solution of erythromycin, propylene glycol, ethyl alcohol, and an ethoxylated ether of lauryl alcohol.

2. A composition as defined in claim 1 comprising from about 0.5 to 3.0% by weight of erythromycin, from about 35 to 45% by weight of propylene glycol, from about 4 to 10% by weight of ethoxylated ether of lauryl alcohol, and an amount of ethyl alcohol sufficient to make up 100% of solution.

3. A composition as defined in claim 1 comprising 2% by weight of 100% active erythromycin, 40% by weight of propylene glycol, 6% by weight of ethoxylated ether of lauryl alcohol having the formula $CH_3(CH_2)_{10}CH_2-(OCH_2CH_2)nOH$ wherein n has an average value of 4, the remainder of the solution consisting of specially denatured alcohol.

* * * * *

UNITED STATES PATENT OFFICE
CERTIFICATE OF CORRECTION

Patent No. 4,000,263      Dated December 28, 1976

Inventor(s) Peter Hebborn

It is certified that error appears in the above-identified patent and that said Letters Patent are hereby corrected as shown below:

Column 2, line 36, "R" should read -- n --.

Signed and Sealed this

Eighth Day of March 1977

[SEAL]

Attest:

RUTH C. MASON
*Attesting Officer*

C. MARSHALL DANN
*Commissioner of Patents and Trademarks*